US009823220B2

(12) United States Patent
Kato et al.

(10) Patent No.: US 9,823,220 B2
(45) Date of Patent: Nov. 21, 2017

(54) NOX CONCENTRATION DETECTION APPARATUS AND NOX CONCENTRATION DETECTION METHOD

(75) Inventors: Kenji Kato, Nagoya (JP); Kouji Shiotani, Kasugai (JP); Takeshi Kawai, Komaki (JP); Satoshi Teramoto, Nisshin (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 1331 days.

(21) Appl. No.: 13/398,095

(22) Filed: Feb. 16, 2012

(65) Prior Publication Data

US 2012/0211374 A1    Aug. 23, 2012

(30) Foreign Application Priority Data

Feb. 17, 2011 (JP) .................................. 2011-32651

(51) Int. Cl.
*G01N 27/419*    (2006.01)

(52) U.S. Cl.
CPC .................................. *G01N 27/419* (2013.01)

(58) Field of Classification Search
CPC .. G01M 15/10; G01M 15/102; G01M 15/104; G01N 27/417–27/419;
(Continued)

(56) References Cited

U.S. PATENT DOCUMENTS 8,197,652 B2 * 6/2012 Horisaka et al. ............. 204/427

FOREIGN PATENT DOCUMENTS

EP    0791827 A1    8/1997
JP    9-288084 A    11/1997
(Continued)

OTHER PUBLICATIONS

Japanese Office Action dated Mar. 19, 2013 for corresponding Japanese Patent Application No. JP 2011-032651.

(Continued)

*Primary Examiner* — Luan Van
*Assistant Examiner* — Maris R Kessel
(74) *Attorney, Agent, or Firm* — Sughrue Mion, PLLC

(57) ABSTRACT

An apparatus and method for individually detecting NO and $NO_2$ concentrations as $NO_X$-components of an object gas. An NO concentration corresponding value is obtained from a first detection element not having a reduction section. An NO concentration corresponding value is obtained from a second detection element having a reduction section, and having an $NO_2/NO$ sensitivity ratio greater than that of the first detection element. The difference $\Delta C$ between the NO concentration corresponding values of the two detection elements is obtained, and divided by the difference $\Delta S$ between the $NO_2/NO$ sensitivity ratios of the two detection elements, whereby an $NO_2$ concentration corresponding value is obtained. A value obtained by multiplying the $NO_2$ concentration corresponding value by the $NO_2/NO$ sensitivity ratio of the second detection element is subtracted from the NO concentration corresponding value of the second detection element, whereby an NO concentration corresponding value is obtained.

3 Claims, 4 Drawing Sheets

(58) Field of Classification Search
CPC .............. G01N 1/2252; F01N 2560/00; F01N 2560/02; F01N 2560/026; F01N 2560/20
USPC ................. 204/410, 411, 421–429; 205/781, 205/783.5–785, 787; 73/23.31, 23.32
See application file for complete search history.

(56) References Cited

FOREIGN PATENT DOCUMENTS

| | | |
|---|---|---|
| JP | 9-297119 A | 11/1997 |
| JP | 11-311613 A | 11/1999 |

OTHER PUBLICATIONS

Nobuhide Kato, et al.; "Thick Film ZRO$_2$ NO$_x$ Sensor"; SAE Technical Paper Series 960334; Reprinted from: Electronic Engine Controls 1996 (SP-1149); Copyright 1996 Society of Automotive Engineers, Inc.; International Congress & Exposition, Detroit, Michigan, Feb. 26-29, 1996.

* cited by examiner

NOX CONCENTRATION DETECTION APPARATUS AND NOX CONCENTRATION DETECTION METHOD

BACKGROUND OF THE INVENTION

1. Field of the Invention

The present invention relates to an apparatus and a method for detecting the concentration of $NO_X$ contained in a gas to be detected (hereinafter referred to as an "object gas").

2. Description of the Related Art

A detection element has been known whose output changes with the concentration of a specific gas (oxygen, $NO_X$, etc.) contained in exhaust gas discharged from an internal combustion engine such as an automotive engine. For example, a detection element capable of detecting the concentration of $NO_X$ has a layered structure including at least one pump cell composed of a solid electrolyte member and a pair of electrodes provided thereon. The detection element includes a first measurement chamber (first internal cavity) into which exhaust gas is introduced via a diffusion resistor section (first diffusion path); and a second measurement chamber (second internal cavity) into which exhaust gas, whose oxygen has been pumped out in the first measurement chamber, is introduced (for example, see Non-patent Document 1).

Oxygen contained in the exhaust gas introduced into the first measurement chamber is pumped out of the first measurement chamber to the outside by a first pump cell, whereby the concentration of oxygen remaining in the exhaust gas introduced into the second measurement chamber is adjusted to a predetermined low level. $NO_X$ contained in exhaust gas includes NO and $NO_2$. According to Non-patent Document 1, most of the $NO_2$ is reduced to NO in the first measurement chamber. In the second measurement chamber, NO is decomposed to nitrogen and oxygen by the catalytic action of an electrode formed of noble metal such as Pt or Rh. At that time, oxygen derived from the decomposed NO (oxygen as a constituent of NO or $NO_2$ ($NO_X$)) is pumped out by a second pump cell. In the second pump cell, electrons conveyed via oxygen ions are detected in the form of a current. The oxygen concentration detected in this manner is offset by the concentration of residual oxygen (the above-mentioned adjusted oxygen concentration), whereby the concentration of $NO_X$-originating oxygen (ultimately, the concentration of $NO_X$) is detected.

[Non-patent Document 1] N. Kato et al., "Thick Film $ZrO_2$ $NO_X$ Sensor", SAE Technical paper series 960334 (1996)

3. Problems to be Solved by the Invention

However, the detection element merely detects the concentration of $NO_X$; i.e., the mixture of NO and $NO_2$, and cannot detect the concentration of NO and the concentration of $NO_2$ individually.

SUMMARY OF THE INVENTION

The present invention has been accomplished in order to solve the above-described problems, and an object thereof is to provide an apparatus and a method for individually detecting the concentrations of NO and $NO_2$, which makeup $NO_X$ contained in an object gas.

The above object has been achieved in accordance with a first aspect (1) of the invention, by providing an $NO_X$ concentration detection apparatus comprising a first element section through which current corresponding to the concentration of $NO_X$ in an object gas flows and which has a first sensitivity ratio between sensitivity to NO concentration and sensitivity to $NO_2$ concentration; a second element section through which current corresponding to the concentration of $NO_X$ contained in the object gas flows and which has a second sensitivity ratio between sensitivity to NO concentration and sensitivity to $NO_2$ concentration, the second sensitivity ratio being greater than the first sensitivity ratio; first obtaining means for obtaining a first concentration corresponding value which corresponds to the concentration of NO on the basis of the magnitude of the current flowing through the first element section; second obtaining means for obtaining a second concentration corresponding value which corresponds to the concentration of NO on the basis of the magnitude of the current flowing through the second element section; first calculation means for calculating a concentration difference, which is the difference between the first concentration corresponding value and the second concentration corresponding value; second calculation means for calculating a sensitivity difference, which is the difference between the first sensitivity ratio and the second sensitivity ratio, and for calculating an $NO_2$ concentration corresponding value corresponding to the concentration of $NO_2$ contained in the object gas on the basis of the concentration difference and the sensitivity difference; and third calculation means for calculating an NO concentration corresponding value corresponding to the concentration of NO in the object gas on the basis of the first concentration corresponding value or the second concentration corresponding value, and the $NO_2$ concentration corresponding value.

In the above first aspect of the invention, the concentration of $NO_X$ is detected through use of two element sections; i.e., a first element section which has a first sensitivity ratio, which is the ratio between sensitivity to NO concentration and sensitivity to $NO_2$ concentration, and a second element section which has a second sensitivity ratio greater than the first sensitivity ratio, whereby the concentrations of NO and $NO_2$, which constitute $NO_X$ contained in the object gas, can be obtained individually. Specifically, since the difference in sensitivity ratio between the first element section and the second element section is produced due to their difference in sensitivity to $NO_2$ among $NO_X$ components, the $NO_2$ concentration corresponding value corresponding to the concentration of $NO_2$ can be obtained on the basis of the concentration. Namely, this is the difference between the concentration corresponding values obtained from the first element section and the second element section, and the sensitivity difference, which is the difference in sensitivity between the first element section and the second element section. For example, the $NO_2$ concentration corresponding value can be calculated by dividing the concentration difference by the sensitivity difference. Then, the NO concentration corresponding value corresponding to the concentration of NO can be obtained on the basis of the first concentration corresponding value obtained by the first obtaining means or the second concentration corresponding value obtained by the second obtaining means, and the $NO_2$ concentration corresponding value corresponding to the concentration of $NO_2$. For example, a value obtained by multiplying the $NO_2$ concentration corresponding value by the first sensitivity ratio (or the second sensitivity ratio) is subtracted from the first concentration corresponding value (or the second concentration corresponding value), whereby the NO concentration corresponding value can be finally obtained. As described above, through application of the present invention, the concentrations of NO and $NO_2$ can be obtained individually. The present invention therefore differs from the prior art technique which encounters difficulty in individually obtaining the concentrations of NO and $NO_2$, although it can obtain the overall concentration of $NO_X$.

In a preferred embodiment of the $NO_X$ concentration detection apparatus according to (1) above, the $NO_X$ concentration detection apparatus is configured such that the first element section is a first detection element comprising a first measurement chamber into which the object gas is introduced via a first diffusion resistor section which restricts flow of the object gas therethrough, a first oxygen pump cell having a first solid electrolyte layer and a pair of first electrodes provided on the inner and outer sides of the first measurement chamber, a second measurement chamber which is located downstream of the first measurement chamber and into which the object gas is introduced from the first measurement chamber, and a second oxygen pump cell having a second solid electrolyte layer and a pair of second electrodes provided on the inner and outer sides of the second measurement chamber; and the second element section is a second detection element comprising a third measurement chamber into which the object gas is introduced via a second diffusion resistor section which restricts flow of the object gas therethrough, a third oxygen pump cell having a third solid electrolyte layer and a pair of third electrodes provided on the inner and outer sides of the third measurement chamber, a fourth measurement chamber which is located downstream of the third measurement chamber and into which the object gas is introduced from the third measurement chamber, a fourth oxygen pump cell having a fourth solid electrolyte layer and a pair of fourth electrodes provided on the inner and outer sides of the fourth measurement chamber, a reduction section provided upstream of the second diffusion resistor section, said reduction section reducing $NO_2$ contained in the object gas introduced into the third measurement chamber to NO, and a heater for heating the reduction section. In this case, the $NO_X$ concentration detection apparatus comprises a first element control section which controls the first detection element, the first element control section controlling the supply of electric current to the first oxygen pump cell so as to pump out oxygen contained in the object gas introduced into the first measurement chamber or pump oxygen thereinto, to thereby control the oxygen concentration within the first measurement chamber to a constant level, and the first element control section applying a voltage to the second oxygen pump cell to thereby control decomposition of $NO_X$ contained in the object gas and pumping out of dissociated oxygen from the second measurement chamber; a second element control section which controls the second detection element, the second element control section controlling the supply of electric current to the third oxygen pump cell so as to pump out oxygen contained in the object gas introduced into the third measurement chamber or pump oxygen thereinto, to thereby control the oxygen concentration within the third measurement chamber to a constant level, and the second element control section applying a voltage to the fourth oxygen pump cell to thereby control decomposition of $NO_X$ contained in the object gas and pumping out of dissociated oxygen from the fourth measurement chamber; and a heater control section which supplies a drive current to the heater so as to heat the object gas flowing through the reduction section at least to a reduction temperature required for reducing $NO_2$ to NO.

In the above preferred embodiment (2), since the reduction section is provided upstream of the second diffusion resistor section of the second element section, $NO_2$ is directed to pass through the second diffusion resistor section after having been reduced to NO. That is, when the object gas is introduced into the third measurement chamber, the speed at which $NO_2$ passes through the second diffusion resistor section does not become a limiting factor for detecting the concentration of $NO_X$. Therefore, the detection sensitivity to the concentration of $NO_X$ (that is, the sensitivity ratio between sensitivity to the concentration of NO and sensitivity to the concentration of $NO_2$) of the second element section can be made different from the detection sensitivity to the concentration of $NO_X$ (that is, the sensitivity ratio between sensitivity to the concentration of NO and sensitivity to the concentration of $NO_2$) of the first element section. As described above, in the first aspect (1), by providing the first element section and the second element section having different sensitivity ratios, the concentration of NO and the concentration of $NO_2$ can be readily obtained individually.

In a second aspect (2), the present invention provides a method for detecting $NO_X$ concentration including obtaining the concentrations of NO and $NO_2$ contained in an object gas, which method is executed by a microcomputer provided in a detection apparatus which includes two element sections having different sensitivity ratios, each being a ratio between sensitivity to concentrations of NO and $NO_2$ contained in the object gas, said method comprising: obtaining a first concentration corresponding value corresponding to the concentration of NO on the basis of the magnitude of current flowing through a first element section having a first sensitivity ratio (first obtaining step); obtaining a second concentration corresponding value corresponding to the concentration of NO on the basis of the magnitude of current flowing through a second element section having a second sensitivity ratio greater than the first sensitivity ratio (second obtaining step); calculating a concentration difference, which is the difference between the first concentration corresponding value and the second concentration corresponding value (first calculation step); calculating a sensitivity difference, which is the difference between the first sensitivity ratio and the second sensitivity ratio, and calculating an $NO_2$ concentration corresponding value corresponding to the concentration of $NO_2$ contained in the object gas on the basis of the concentration difference and the sensitivity difference (second calculation step); and calculating an NO concentration corresponding value corresponding to the concentration of NO contained in the object gas on the basis of the first concentration corresponding value or the second concentration corresponding value, and the $NO_2$ concentration corresponding value (third calculation step).

In the above second aspect, the concentration of $NO_X$ is detected through use of two element sections; i.e., a first element section which has a first sensitivity ratio, which is the ratio between sensitivity to concentration of NO and that to concentration of $NO_2$, and a second element section which has a second sensitivity ratio greater than the first sensitivity ratio, whereby the concentrations of NO and $NO_2$, which constitute $NO_X$ contained in the object gas, are obtained individually. Specifically, since the difference in sensitivity ratio between the first element section and the second element section is produced due to their difference in sensitivity to $NO_2$ among $NO_X$ components, the $NO_2$ concentration corresponding value corresponding to the concentration of $NO_2$ can be obtained on the basis of the concentration difference, which is the difference between the concentration corresponding values obtained from the first element section and the second element section, and the sensitivity difference, which is the difference in sensitivity between the first element section and the second element section. For example, the $NO_2$ concentration corresponding value can be calculated by dividing the concentration difference by the sensitivity difference. Then, the NO concentration corresponding value corresponding to the concentration of NO can be obtained on the basis of the first concentration corresponding value obtained by the first obtaining step or the second concentration corresponding value obtained by the second obtaining step, and the $NO_2$ concentration corresponding value corresponding to the concentration of $NO_2$. For example, a value obtained by multiplying the $NO_2$ concentration corresponding value by the first sensitivity ratio (or the second sensitivity ratio) is subtracted from the first concentration corresponding value (or the second concentration corresponding value), whereby the NO concentration corresponding value can be finally obtained. As described above, through application of the present invention, the concentrations of NO and $NO_2$ can be obtained individually. The present invention therefore differs from the prior art technique which encounters difficulty in individually obtaining the concentrations of NO and $NO_2$, although the prior art technique can obtain the overall concentration of $NO_X$.

DESCRIPTION OF REFERENCE NUMERALS

Figure 1:
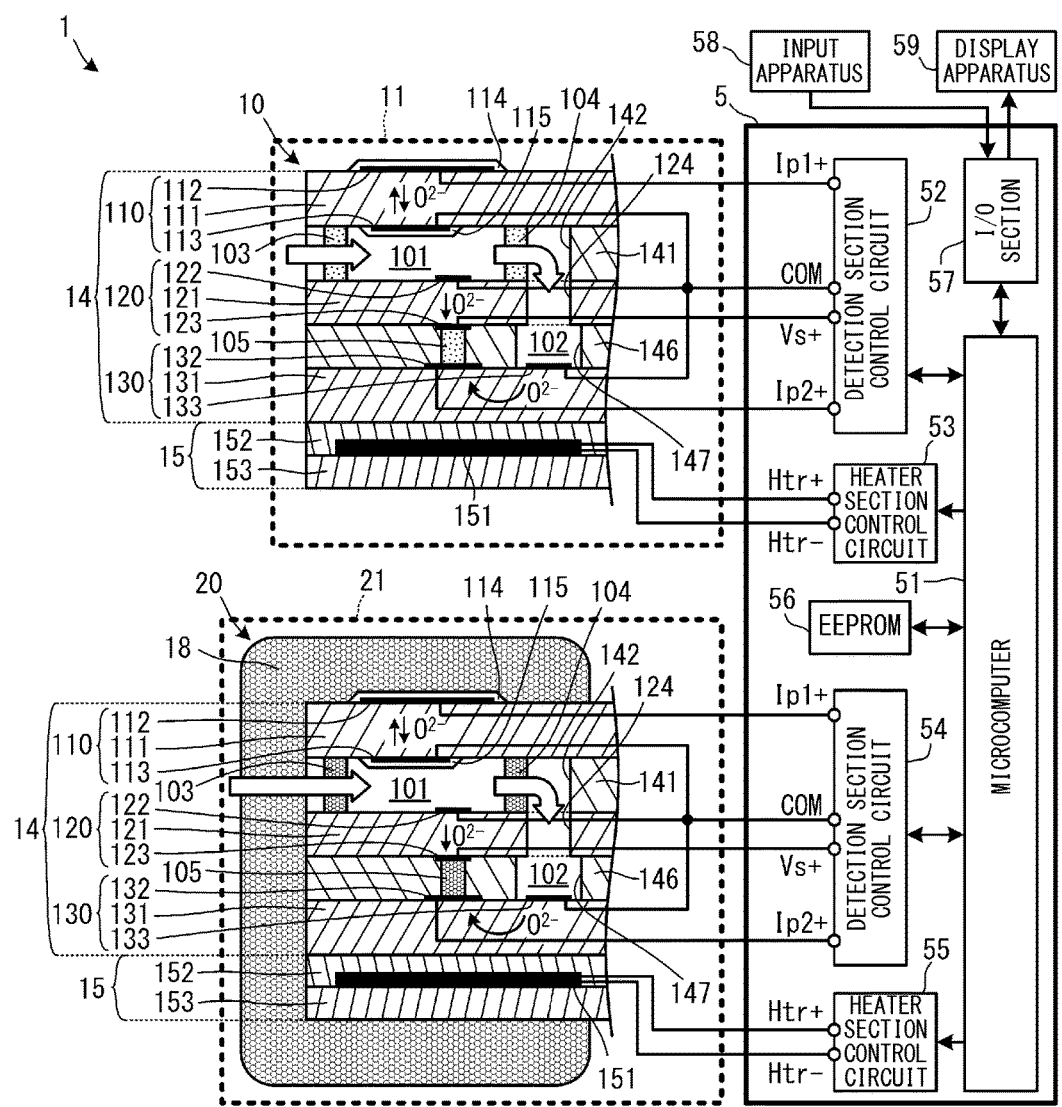
FIG. 1 is a diagram which schematically shows the configuration of a detection apparatus 1 including a first detection element 10 and a second detection element 20.

Various reference numerals used to identify structural features in the drawings including the following.
1: detection apparatus
10, 20: detection element
18: reduction section
51: microcomputer
52, 54: detection section control circuit
53, 55: heater section control circuit
101: first measurement chamber
102: second measurement chamber
103, 104: diffusion resistor section
110: Ip1 cell
111, 131: solid electrolyte member
112, 113, 132, 133: electrode
130: Ip2 cell
151: heater conductor

DETAILED DESCRIPTION OF THE PREFERRED EMBODIMENTS

An $NO_X$ concentration detection apparatus and an $NO_X$ concentration detection method according to one embodiment of the present invention will now be described with reference to the drawings. However, the present invention should not be construed as being limited thereto.

First, the configuration of a detection apparatus 1, which is an example of the $NO_X$ concentration detection apparatus, will be described with reference to FIG. 1. FIG. 1 is a diagram schematically showing the configuration of the detection apparatus 1 including a first detection element 10 and a second detection element 20. The first detection element 10 is an $NO_X$ concentration detection element which is incorporated in an ordinary $NO_X$ sensor (not shown) and through which current flows. This current corresponds to the concentration of $NO_X$ contained in an object gas, such as exhaust gas. The first detection element 10 has the form of a slender, elongated plate. Similarly, the second detection element 20 is an $NO_X$ concentration detection element having a platelike shape, and is identical with the first detection element 10 except that the second detection element 20 has a reduction section 18, described below. In FIG. 1, the first detection element 10 and the second detection element 20 are illustrated by cross-sectional views showing the internal structures of front end portions of the two detection elements; and portions common between the first detection element 10 and the second detection element 20 are denoted by the same reference numerals. Accordingly, in the following description, portions of the second detection element 20 which are structurally identical with those of the first detection element 10 will be described in the description of the first detection element 10; and only portions of the second detection element 20 which structurally differ from those of the first detection element 10 will be described separately.

In the detection apparatus 1 of the present embodiment, the first detection element 10 and the second detection element 20 are individually accommodated in ordinary housings 11 and 21, whereby two separate $NO_X$ sensors are formed (see FIG. 1). These housings 11 and 21 are attached to, for example, the exhaust pipe of an automobile, for detecting the concentration of $NO_X$ contained in an object gas, such as exhaust gas (for separately detecting the concentrations of NO and $NO_2$ as described below). Needless to say, the first detection element 10 and the second detection element 20 may be accommodated in a single housing and used for detecting the concentration of $NO_X$.

The detection apparatus 1 shown in FIG. 1 is composed of the first detection element 10, the second detection element 20, and a sensor control section 5 which controls the first detection element 10 and the second detection element 20, and which calculates the concentration of $NO_X$. The sensor control section 5 includes a known microcomputer 51 containing a CPU, ROM, and RAM; a detection section control circuit 52 and a heater section control circuit 53 for controlling the drive of the first detection element 10; a detection section control circuit 54 and a heater section control circuit 55 for controlling the drive of the second detection element 20. The detection section control circuits 52 and 54 generate currents for driving respective gas detection sections 14 (described below) of the first detection element 10 and the second detection element 20. Similarly, the heater section control circuits 53 and 55 generate currents for driving respective heater sections 15 (described below) of the first detection element 10 and the second detection element 20. The detection section control circuit 52 and the heater section control circuit 53 cooperate with the microcomputer 51 so as to control the drive of the first detection element 10 in the same manner as that of a known sensor controller. Similarly, the detection section control circuit 54 and the heater section control circuit 55 cooperate with the microcomputer 51 so as to control the drive of the second detection element 20 in the same manner as that of a known sensor controller. Therefore, in the following description, description of the configurations and operations of the detection section control circuits 52 and 54 and the heater section control circuits 53 and 55 will be omitted or simplified.

An EEPROM 56 is connected to the microcomputer 51. The $NO_2/NO$ sensitivity ratio (the ratio between the sensitivity to NO and the sensitivity to $NO_2$) previously obtained for each of the first detection element 10 and the second detection element 20 is stored in the EEPROM 56. The sensor control section 5 includes an input/output section 57 which enables operation of the detection apparatus 1 from an input apparatus 58, such as a console, and enables display of the detected $NO_X$ concentration on a display apparatus 59.

Next, the first detection element 10 will be described. The first detection element 10 includes the gas detection section 14 for detecting the concentration of $NO_X$ and the heater section 15 for heating the gas detection section 14 for quick activation. The gas detection section 14 and the heater section 15 are stacked together for unification.

The gas detection section 14 has a layered structure in which three platelike solid electrolyte members 111, 121, and 131, and two insulators 141 and 146 formed of alumina or the like are alternately stacked. The gas detection section 14 has a first measurement chamber 101, a second measurement chamber 102, a reference oxygen chamber 105, an Ip1 cell (oxygen pump cell) 110, a Vs cell (oxygen partial pressure detection cell) 120, and an Ip2 cell (oxygen pump cell) 130.

The first measurement chamber 101 is a small space within the gas detection section 14 into which the object gas is first introduced. The first measurement chamber 101 is formed between the solid electrolyte member 111 and the solid electrolyte member 121. Electrodes 113 and 122 are disposed in the first measurement chamber 101 to be located on the solid electrolyte member 111 and the solid electrolyte member 121, respectively.

A diffusion resistor section 103, which is a porous body formed of a ceramic material such as alumina and having a plurality of continuous pores, is provided in the first measurement chamber 101 to be located at the front end of the gas detection section 14. The diffusion resistor section 103 functions as a partition between the exterior and interior of the first measurement chamber 101, and restricts the amount per unit time of flow of the object gas into the first measurement chamber 101. Similarly, a diffusion resistor section 104, which is a porous body formed of a ceramic material such as alumina and having a plurality of continuous pores, is provided in the first measurement chamber 101 to be located on the side toward the rear end of the gas detection section 14. The diffusion resistor section 104 functions as a partition between the first measurement chamber 101 and the second measurement chamber 102, and restricts the amount per unit time of flow of the object gas from the first measurement chamber 101 into the second measurement chamber 102.

The second measurement chamber 102 is a small space surrounded by the solid electrolyte member 111, the diffusion resistor section 104, the wall surface of an opening 142 of the insulator 141, the wall surface of an opening 124 of the solid electrolyte member 121, the wall surface of an opening 147 of the insulator 146, and the solid electrolyte member 131. The second measurement chamber 102 communicates with the first measurement chamber 101 via the diffusion resistor section 104. The object gas whose oxygen concentration has been adjusted by the Ip1 cell 110 is introduced into the second measurement chamber 102. An electrode 133 is disposed on the upper surface of the solid electrolyte member 131 that is exposed to the second measurement chamber 102.

The reference oxygen chamber 105 is a small space which is surrounded by the wall surface of an opening provided in the insulator 146 independently of the second measurement chamber 102, the solid electrolyte member 121, and the solid electrolyte member 131. In the reference oxygen chamber 105, an electrode 123 is disposed on the surface of the solid electrolyte member 121, and an electrode 132 is disposed on the surface of the solid electrolyte member 131. A porous body formed of a ceramic material fills the reference oxygen chamber 105.

The Ip1 cell 110 includes the solid electrolyte member 111, and a pair of porous electrodes 112 and 113. The solid electrolyte member 111 is formed of, for example, zirconia, and has oxygen-ion conductivity. The electrodes 112 and 113 are provided on opposite surfaces of the solid electrolyte member 111 with respect to the stacking direction of the first detection element 10. The electrode 113 is disposed in the first measurement chamber 101 as described above, and the electrode 112 is disposed at a position corresponding to the electrode 113 with the solid electrolyte member 111 intervening between the two electrodes. The electrodes 112 and 113 are formed of a material whose predominant component is Pt. Examples of the material whose predominant component is Pt include Pt, Pt alloy, and cermet containing Pt and ceramic. Porous protection layers 114 and 115 formed of ceramic are formed on the surfaces of the electrodes 112 and 113, respectively. The electrode 112 of the Ip1 cell 110 is connected to an Ip1+ port of the detection section control circuit 52 of the sensor control section 5, and the electrode 113 of the Ip1 cell 110 is connected to a COM port (reference potential) of the detection section control circuit 52.

The Vs cell 120 includes the solid electrolyte member 121, and a pair of porous electrodes 122 and 123. The solid electrolyte member 121 is formed of, for example, zirconia, and has oxygen-ion conductivity. The solid electrolyte member 121 is disposed to face the solid electrolyte member 111 with the insulator 141 intervening therebetween. The electrodes 122 and 123 are provided on opposite surfaces of the solid electrolyte member 121 with respect to the stacking direction of the first detection element 10. The electrode 123 is disposed in the reference oxygen chamber 105 as described above, and the electrode 122 is disposed in the first measurement chamber 101 at a position corresponding to the electrode 123, with the solid electrolyte member 121 intervening between the two electrodes. The electrodes 122 and 123 are formed of the above-described material whose predominant component is Pt. The electrode 122 of the Vs cell 120 is connected to the COM port of the detection section control circuit 52, and the electrode 123 of the Vs cell 120 is connected to a Vs+ port of the detection section control circuit 52.

The Ip2 cell 130 includes the solid electrolyte member 131, and a pair of porous electrodes 132 and 133. The solid electrolyte member 131 is formed of, for example, zirconia, and has oxygen-ion conductivity. The solid electrolyte member 131 is disposed to face the solid electrolyte member 121 with the insulator 146 intervening therebetween. The electrodes 132 and 133 are provided on the surface of the solid electrolyte member 131 located on the side toward the solid electrolyte member 121 with respect to the stacking direction of the first detection element 10. The electrode 133 is disposed in the second measurement chamber 102 as described above, and the electrode 132 is disposed in the reference oxygen chamber 105 such that the solid electrolyte member 131 intervenes between the paired electrodes 132 and 133. The electrodes 132 and 133 are formed of the above-described material whose predominant component is Pt. The electrode 132 of the Ip2 cell 130 is connected to an Ip2+ port of the detection section control circuit 52, and the electrode 133 of the Ip2 cell 130 is connected to the COM port of the detection section control circuit 52.

As described above, the heater section 15 is provided on the outer side (lower side in FIG. 1) of the solid electrolyte member 131 of the gas detection section 14. The heater section 15 includes insulation layers 152 and 153, and a heater conductor 151. The insulation layers 152 and 153 are mainly formed of alumina and have a sheetlike shape. The heater conductor 151 is a single, continuous electrode buried between the insulation layers 152 and 153. The heater conductor 151 is formed of a material whose predominant component is Pt, and has a correlation between its temperature and its resistance. One end of the heater conductor 151 is connected to an Htr− port of the heater section control circuit 53, whereby the one end is grounded. The other end of the heater conductor 151 is connected to an Htr+ port of the heater section control circuit 53. The heater section control circuit 53 controls the duty ratio of an ON/OFF signal supplied to the Htr+ port in accordance with the impedance of the gas detection section 14 (more specifically, the impedance periodically obtained at the Vs cell 120), to thereby control the electrical power supplied from a battery power source to the heater conductor 151, whereby the heating temperature of the heater section 15 is adjusted.

Next, the second detection element 20 will be described. As described above, the structure of the second detection element 20 differs from that of the first detection element 10 in that the second detection element 20 has the reduction section 18. Except for this difference, the second detection element 20 is identical in structure with the first detection element 10, and includes the gas detection section 14 for detecting the concentration of $NO_X$, and the heater section 15 for heating the gas detection section 14 for quick activation.

The reduction section 18 is a porous body formed of a ceramic material such as alumina and having a plurality of continuous pores, and is provided at a front end portion of the second detection element 20. The reduction section 18 covers the circumference of the front end portion (including the front end surface) of the second detection element 20 such that the reduction section 18 is disposed on the upstream side of the diffusion resistor section 103 on a path through which the object gas is introduced into the first measurement chamber 101 of the second detection element 20. The porosity of the reduction section 18 is higher than that of the diffusion resistor section 103. A porous body has a plurality of continuous pores for allowing gas to pass therethrough, and its porosity is the ratio of the volume of all spaces formed by the pores to the volume of the entire porous body including the pores. The lower the porosity, the greater the flow resistance acting on gas flowing (passing) through the porous body. The diffusion resistor section 103 is provided so as to produce a flow resistance which limits the introduction speed of the object gas to thereby prevent limitless introduction of the object gas into the first measurement chamber 101. In contrast, the reduction section 18 is provided to serve as a place where, of $NO_X$ contained in the object gas, $NO_2$ undergoes a reduction reaction. Therefore, the reduction section 18 has a porosity which is higher than that of the diffusion resistor section 103 and which is determined such that the reduction section 18 does not hinder the flow of the object gas. Notably, the porosity of the reduction section 18 can be rendered higher than that of the diffusion resistor section 103 by adjusting the grain sizes of the material powders of ceramics which constitute intermediates which will become the reduction section 18 and the diffusion resistor section 103 through firing, or by adjusting the amount of a binder contained in the intermediates. Alternatively, in the case where a pore-forming agent which will form pores after firing is contained in the intermediates, the amount of the pore-forming agent is adjusted.

The electrode 112 of the Ip1 cell 110 of the second detection element 20 is connected to an Ip1+ port of the detection section control circuit 54 of the sensor control section 5, and the electrode 113 of the Ip1 cell 110 is connected to a COM port (reference potential) of the detection section control circuit 54. The electrode 122 of the Vs cell 120 is connected to the COM port of the detection section control circuit 54, and the electrode 123 of the Vs cell 120 is connected to a Vs+ port of the detection section control circuit 54. The electrode 132 of the Ip2 cell 130 is connected to an Ip2+ port of the detection section control circuit 54, and the electrode 133 of the Ip2 cell 130 is connected to the COM port of the detection section control circuit 54. Also, one end of the heater conductor 151 of the second detection element 20 is connected to an Htr− port of the heater section control circuit 55, the other end of the heater conductor 151 is connected to an Htr+ port of the heater section control circuit 55.

Next, operation of the detection apparatus 1 will be described. However, beforehand, operations of the first detection element 10 and the second detection element 20 for detecting the concentration of $NO_X$ will be described briefly. Notably, since the operation of the first detection element 10 for detecting the concentration of $NO_X$ is identical with that of the second detection element 20, in this embodiment, only operation of the first detection element 10, which is driven and controlled by the detection section control circuit 52 and the heater section control circuit 53 of the sensor control section 5, will be described.

The solid electrolyte members 111, 121 and 131, which constitute the gas detection section 14 of the first detection element 10, are activated by being heated. The heater section control circuit 53 controls the current flowing between the Htr+ port and the Htr− port so as to quickly activate the solid electrolyte members 111, 121 and 131. After activation is completed, the heater section control circuit 53 controls the supply of electric current to the heater section 15 so as to maintain the gas detection section 14 at a predetermined temperature.

The object gas (e.g., exhaust gas) is introduced into the housing 11 of the $NO_X$ sensor (specifically, a portion (protector) of the housing 11 which covers the circumference of a front end portion of the first detection element 10 or the second detection element 20 and which has a gas introduction opening). When the object gas reaches the circumference of the first detection element 10, the object gas is introduced into the first measurement chamber 101 through the diffusion resistor section 103. The detection section control circuit 52 supplies a very small constant current from the Vs+ port such that the oxygen partial pressure within the reference oxygen chamber 105 becomes a predetermined level, to thereby pump (move) oxygen from the electrode 122 side toward the electrode 123 side via the solid electrolyte member 121. Thus, the electrode 123 of the Vs cell 120 serves as a reference electrode exposed to oxygen of a reference concentration. When the oxygen partial pressure within the object gas introduced into the first measurement chamber 101 differs from the oxygen partial pressure within the reference oxygen chamber 105, oxygen ions move between the first measurement chamber 101 and the reference oxygen chamber 105 via the Vs cell 120 such that the two oxygen partial pressures are balanced, whereby a voltage (electromotive force) is generated between the electrodes 122 and 123.

The detection section control circuit 52 controls the current supplied to the Ip1 cell 110 (Ip1+ port) such that the voltage of the Vs+ port (the voltage generated between the electrodes 122 and 123 of the Vs cell 120) becomes a predetermined voltage (e.g., 425 mV). As a result of this control, pumping oxygen out and in is performed between the atmosphere within the first measurement chamber 101 to which the electrode 113 is exposed and the outside atmosphere to which the electrode 112 of the first detection element 10 is exposed. Thus, the concentration of oxygen contained in the object gas is adjusted to a predetermined low level. Notably, at that time, the concentration of oxygen contained in the object gas can be calculated on the basis of the current flowing through the Ip1 cell 110.

The object gas having an adjusted oxygen concentration is introduced into the second measurement chamber 102 through the diffusion resistor section 104. Within the second measurement chamber 102, NO contained in the object gas is decomposed by means of the catalytic action of the electrode 133 whose predominant component is Pt, whereby $NO_X$-originating oxygen is generated. The $NO_X$-originating oxygen flows between the electrodes 132 and 133 of the Ip2 cell 130 in the form of oxygen ions, whereby an output corresponding to the concentration of $NO_X$ contained in the object gas can be obtained from the Ip2+ port. That is, the output from the Ip2+ port; i.e., the current flowing through the Ip2 cell 130, has a magnitude approximately proportional to the concentration of $NO_X$.

Incidentally, in the second detection element 20, not only the solid electrolyte members 111, 121 and 131 but also the reduction section 18 is heated as a result of heat generated by the heater section 15. For example, when the solid electrolyte members 111, 121 and 131 are heated to a predetermined temperature equal to or higher than 750° C. (activation temperature), as a result of this heating, the reduction section 18 is also heated to a sufficiently high temperature so that the reduction section 18 can heat the object gas, which flows therethrough, to, for example, 650° C. or higher. When the object gas is heated to 650° C. or higher, $NO_2$ contained in the object gas is reduced to NO. As a result, when the object gas passes through the diffusion resistor section 103, the object gas hardly contains $NO_2$, which has a low degree of diffusion (low in passing speed). Therefore, the speed of passage (flow) of $NO_X$ through the diffusion resistor section 103 is not limited by $NO_2$. Also, since $NO_2$ is reduced to NO at the reduction section 18, $NO_2$ need not be reduced to NO within the first measurement chamber 101. Therefore, by providing the reduction section 18, the second detection element 20 can have a higher sensitivity for detection of $NO_X$ (specifically, a higher ratio of sensitivity for $NO_2$ to that for NO), as compared with the first detection element 10 having no reduction section.

The concentration of $NO_X$ is detected in one of three states; i.e., the state in which the object gas does not contain $NO_2$ but contains NO, the case where the object gas does not contain NO but contains $NO_2$, and the case where the object gas contains both of NO and $NO_2$. In the detection apparatus 1 of the present embodiment, irrespective of the state in which the concentration of $NO_X$ is detected, the microcomputer 51 obtains an NO concentration corresponding value associated with a first detection element 10 and an NO concentration corresponding value associated with the second detection element 20 in accordance with an arithmetic expression set for obtaining the NO concentration corresponding values, and on the basis of the currents flowing through the Ip2 cells 130 of the first detection element 10 and the second detection element 20. Since the detection apparatus 1 is configured such that each NO concentration corresponding value is obtained by use of an arithmetic expression set for obtaining the NO concentration corresponding value, the first detection element 10 and the second detection element 20 having the reduction section 18 differ from each other in sensitivity ratio, which is the ratio between sensitivity to NO and sensitivity to $NO_2$, measured under the same NO concentration and the same $NO_2$ concentration.

In the detection apparatus 1 of the present embodiment, the concentration of $NO_X$ contained in the object gas is detected (specifically, the concentration of NO and the concentration of $NO_2$ are detected) through use of the first detection element 10 having no reduction section, and the second detection element 20 having the reduction section 18. In the following, there will be described a process in which the detection apparatus 1 detects the concentrations of NO and $NO_2$ contained in the object gas. Notably, each step of the flowcharts of FIGS. 2 and 3 will be abbreviated to "S." The processing represented by the flowcharts is executed by the CPU of the microcomputer 51.

In the detection apparatus 1, before the concentrations NO and $NO_2$ contained in the object gas are detected, a sensitivity ratio obtaining processing (see FIG. 2) for obtaining an $NO_2$/NO sensitivity ratio, which is the ratio between the sensitivity to NO and the sensitivity to $NO_2$, is performed for each of the first detection element 10 and the second detection element 20. In the present embodiment, this processing is performed before shipping the detection apparatus 1 (in a process of manufacturing the detection apparatus 1) through use of two types of adjusted gases (model gases).

Figure 2:
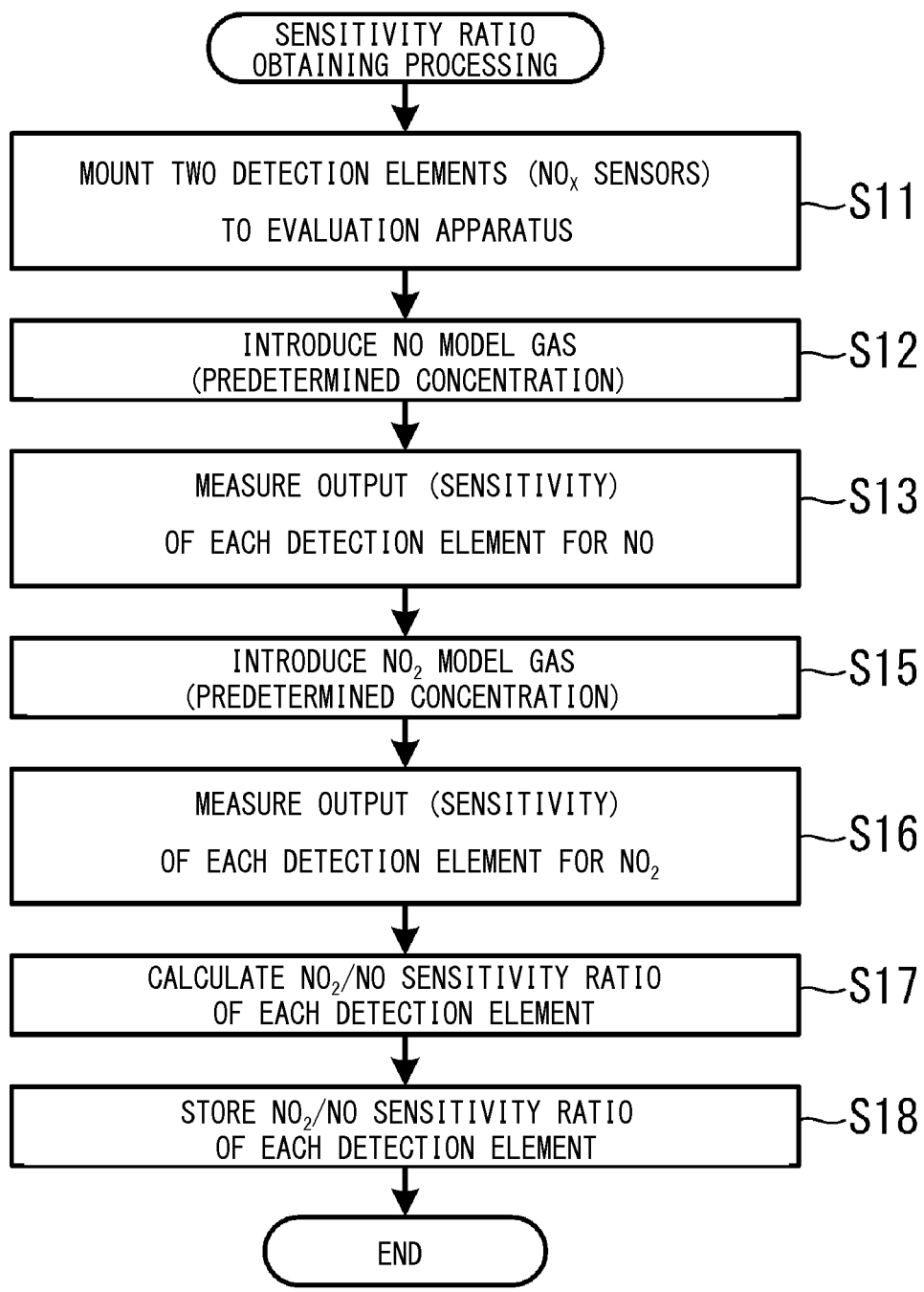
FIG. 2 is a flowchart of sensitivity ratio obtaining processing for obtaining the $NO_2/NO$ sensitivity ratios of the first detection element 10 and the second detection element 20.

The sensitivity ratio obtaining processing shown in FIG. 2 is executed when the input apparatus 58 is operated in accordance with a menu displayed on the display apparatus 59 after power to the detection apparatus 1 is turned on. In accordance with an instruction displayed on the display apparatus 59, the housings 11 and 21, which accommodate the first detection element 10 and the second detection element 20 of the detection apparatus 1, respectively, are mounted to an unillustrated evaluation apparatus (an apparatus which includes a chamber or the like into which the model gases are introduced so as to have the first detection element 10 and the second detection element 20 exposed to the mode gases). After mounting the housings 11 and 21 to the evaluation apparatus, completion of the mounting is reported to the microcomputer 51 through operation of the input apparatus 58 (S11).

The microcomputer 51 sends drive instructs to the detection section control circuits 52 and 54 and the heater section control circuits 53 and 55 so as to activate the solid electrolyte members 111, 121 and 131 of the first detection element 10 and the second detection element 20, to thereby bring them into a state in which they can detect the concentration of $NO_X$. When the detection section control circuits 52 and 54 notify the microcomputer 51 of the fact that the first detection element 10 and the second detection element 20 have been activated, the microcomputer 51 displays on the display apparatus 59 an instruction for prompting introduction of an NO model gas. The NO model gas is a gas whose NO concentration is adjusted to a predetermined level (e.g., 100 ppm) and which does not contain $NO_2$. The evaluation apparatus is then operated so as to supply the NO model gas into the chamber, whereby the first detection element 10 and the second detection element 20 are exposed to the NO model gas (S12). The microcomputer 51 obtains the output values (current values) at the Ip2+ ports of the first detection element 10 and the second detection element 20 from the detection section control circuits 52 and 54 connected to the first detection element 10 and the second detection element 20, respectively. The microcomputer 51 then stores the output values in the RAM as sensitivity to NO of a predetermined concentration (S13). Since the output values become 0 μA when the NO concentration is 0 ppm, a coefficient to be applied to an arithmetic expression for obtaining an NO concentration corresponding value (ppm) from each output value (μA) is calculated on the basis of the output value for the above-described NO model gas, and is stored in the EEPROM 56. Notably, the arithmetic expression, which may be a known one, is stored in the ROM of the microcomputer 51, and the microcomputer 51 obtains the NO concentration corresponding value by using the arithmetic expression, while reading the coefficient thereof out of the EEPROM 56.

Next, the microcomputer 51 displays on the display apparatus 59 an instruction for prompting introduction of an $NO_2$ model gas. The $NO_2$ model gas is a gas whose $NO_2$ concentration is adjusted to a predetermined level (e.g., 100 ppm equal to the NO concentration of the NO model gas) and which does not contain NO. The evaluation apparatus is then operated so as to supply the $NO_2$ model gas into the chamber, whereby the first detection element 10 and the second detection element 20 are exposed to the $NO_2$ model gas (S15). The microcomputer 51 obtains the output values (current values) at the Ip2+ ports of the first detection element 10 and the second detection element 20 from the detection section control circuits 52 and 54 in the same manner as in the above-described case, and stores the output values in the RAM as sensitivity to $NO_2$ of a predetermined concentration (S16).

Next, the microcomputer 51 calculates the $NO_2$/NO sensitivity ratio for each of the first detection element 10 and the second detection element 20 (S17). The $NO_2$/NO sensitivity ratio of the first detection element 10 is calculated by dividing the output value for the $NO_2$ model gas by the output value for the NO model gas, which output values have been stored in the RAM for the first detection element 10, Similarly, the $NO_2$/NO sensitivity ratio of the second detection element 20 is calculated by dividing the output value for the $NO_2$ model gas by the output value for the NO model gas, which output values have been stored in the RAM for the second detection element 20.

In the present embodiment, in consideration of the results obtained in Example 1 described below, the $NO_2$/NO sensitivity ratio (first sensitivity ratio) of the first detection element 10 is assumed to be 0.8 (80%), and the $NO_2$/NO sensitivity ratio (second sensitivity ratio) of the second detection element 20 is assumed to be 1.0 (100%). The calculated $NO_2$/NO sensitivity ratios of the first detection element 10 and the second detection element 20 are stored in the EEPROM 56 (S18). The microcomputer 51 instructs the detection section control circuits 52 and 54 and the heater section control circuits 53 and 55 to stop their drive operations, and ends the sensitivity ratio obtaining processing.

Figure 3:
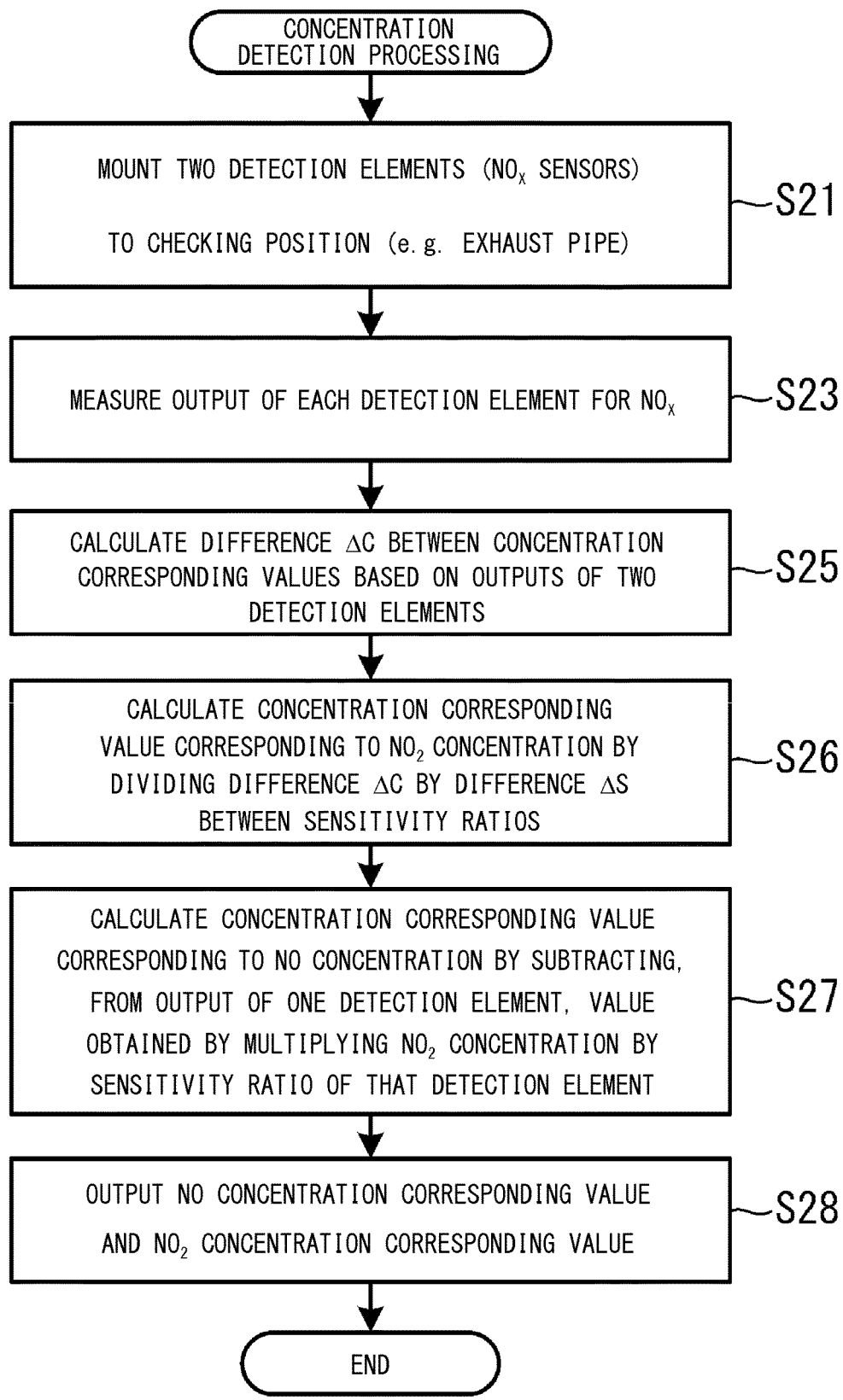
FIG. 3 is a flowchart of concentration detection processing for obtaining the NO concentration and $NO_2$ concentration of an object gas by making use of the first detection element 10 and the second detection element 20.

Next, a process will be described in which the concentrations of NO and $NO_2$ contained in the object gas are detected by the detection apparatus 1. The $NO_2$/NO sensitivity ratios of the first detection element 10 and the second detection element 20, which have been obtained through the sensitivity ratio obtaining processing and stored in the EEPROM 56, are used in concentration detection processing (see FIG. 3). As in the case of the above-described sensitivity ratio obtaining processing, the concentration detection processing shown in FIG. 3 is executed when the input apparatus 58 is operated in accordance with a menu displayed on the display apparatus 59 after the power of the detection apparatus 1 is turned on. In accordance with an instruction displayed on the display apparatus 59, the housings 11 and 21, which accommodate the first detection element 10 and the second detection element 20 of the detection apparatus 1, respectively, are mounted to an unillustrated checking position (e.g., an exhaust pipe through which exhaust gas flows). After mounting the housings 11 and 21, completion of the mounting is reported to the microcomputer 51 through operation of the input apparatus 58 (S21).

As in the case of the above-described sensitivity ratio obtaining processing, the microcomputer 51 sends drive instructions to the detection section control circuits 52 and 54 and the heater section control circuits 53 and 55 so as to activate the first detection element 10 and the second detection element 20. When the detection section control circuits 52 and 54 notify the microcomputer 51 of the fact that the first detection element 10 and the second detection element 20 have been activated, the microcomputer 51 instructs the detection section control circuits 52 and 54 to detect the $NO_X$ concentration of the exhaust gas flowing through the exhaust pipe. The microcomputer 51 obtains the output values (current values) at the Ip2+ ports of the first detection element 10 and the second detection element 20 from the detection section control circuits 52 and 54. Subsequently, for each of the first detection element 10 and the second detection element 20, the microcomputer 51 obtains an NO concentration corresponding value corresponding to the $NO_X$-concentration of the exhaust gas by using the arithmetic expression, which is set for obtaining the NO concentration corresponding value and is stored in the ROM, and while applying thereto the above-described coefficient stored in the EEPROM 56; and the microcomputer 51 stores the NO concentration corresponding value in the RAM (S23).

Next, the microcomputer 51 calculates the difference ΔC between the NO concentration corresponding value of the first detection element 10 and the NO concentration corresponding value of the second detection element 20 (S25). This difference ΔC is a difference produced due to the difference in sensitivity to $NO_2$ between the first detection element 10 and the second detection element 20 (a difference corresponding to the pumping-out amount of $NO_2$-originating oxygen corresponding to the sensitivity difference). Therefore, the microcomputer 51 calculates a difference ΔS between the $NO_2$/NO sensitivity ratios of the first detection element 10 and the second detection element 20, which are stored in the EEPROM 56. Then, by dividing ΔC by ΔS, the microcomputer 51 obtains an $NO_2$ concentration corresponding value corresponding to the concentration of $NO_2$ contained in the exhaust gas for the case where the influence of sensitivity is not present. The microcomputer 51 stores the obtained $NO_2$ concentration corresponding value in the RAM (S26).

Next, the microcomputer 51 obtains an NO concentration corresponding value corresponding to the concentration of NO by subtracting, from the NO concentration corresponding value of the second detection element 20 obtained in S23, a value obtained by multiplying the above-described, calculated $NO_2$ concentration corresponding value by the $NO_2$/NO sensitivity ratio of the second detection element 20 (that is, 1.0). The microcomputer 51 stores the obtained NO concentration corresponding value in the RAM (S27). Notably, in the present embodiment, the $NO_2$/NO sensitivity ratio of the second detection element 20 is 1.0. Therefore, in S27, the NO concentration corresponding value may be calculated by directly subtracting the $NO_2$ concentration corresponding value from the NO concentration corresponding value of the second detection element 20 obtained in S23.

After displaying on the display apparatus 59 the values corresponding to the concentrations of NO and $NO_2$ contained in the exhaust gas, which are obtained in the above-described manner (S28), the microcomputer 51 instructs the detection section control circuits 52 and 54 and the heater section control circuits 53 and 55 to stop their drive operations, and end the concentration detection processing.

As described above, in the detection apparatus 1 of the present embodiment, by providing the reduction section 18, the sensitivity of the second detection element 20 to $NO_2$ can be improved as compared with the first detection element 10 having no reduction section. Thus, a difference in detection sensitivity for $NO_X$ concentration can be provided between the first detection element 10 and the second detection element 20. In this manner, the detection apparatus 1 can detect the concentrations of NO and $NO_2$ contained in the object gas by detecting the concentration of $NO_X$ contained in the object gas through use of the first detection element 10 and the second detection element 20.

As described above, the detection apparatus 1 of the present embodiment separately obtains the concentrations of NO and $NO_2$, which are $NO_X$ components contained in the object gas, by detecting the concentrations of $NO_X$ through use of two detection elements; i.e., the first detection element 10 whose sensitivity ratio between sensitivity to NO and that to $NO_2$ is 0.8 (first sensitivity ratio), and the second detection element 20 whose sensitivity ratio between sensitivity to NO and that to $NO_2$ is 1.0 (second sensitivity ratio) greater than the first sensitivity ratio. Specifically, since the difference in sensitivity ratio between the first detection element 10 and the second detection element 20 arises because of their difference in sensitivity to $NO_2$ among $NO_X$ components, an output value corresponding to the concentration of $NO_2$ ($NO_2$ concentration corresponding value) can be obtained on the basis of the difference $\Delta C$. $\Delta C$ is the difference between the NO concentration corresponding values obtained from the first detection element 10 and the second detection element 20, respectively, and the difference $\Delta S$ between the $NO_2$/NO sensitivity ratios of the first detection element 10 and the second detection element 20. Then, the value corresponding to the concentration of NO contained in the object gas can be finally obtained on the basis of the NO concentration corresponding value obtained from the first detection element 10 or the NO concentration corresponding value obtained from the second detection element 20, and the $NO_2$ concentration corresponding value obtained as described above. As described above, through application of the present invention, the concentrations of NO and $NO_2$ can be individually obtained. The present invention therefore differs from the prior art technique which encounters difficulty in individually obtaining the concentrations of NO and $NO_2$, although the prior art technique can obtain the overall concentration of $NO_X$.

Notably, the present invention is not limited to the above-described embodiment, and may be modified in various ways. For example, in the above-described embodiment, the first detection element 10 has an $NO_2$/NO sensitivity ratio of 0.8, and the second detection element 20 has an $NO_2$/NO sensitivity ratio of 1.0. However, the combination of sensitivity ratios can be set freely. For example, a detection element having an $NO_2$/NO sensitivity ratio of 0.7 and a detection element having an $NO_2$/NO sensitivity ratio of 0.9 may be used as the first detection element 10 and the second detection element 20, respectively.

Also, the process (computation method) for computing the NO concentration and the $NO_2$ concentration shown in S25 to S27 of the concentration detection processing (FIG. 3) is a mere example, and these concentrations may be obtained by other computation processes. Moreover, although the sensor control section 5 of the detection apparatus 1 includes two sets of the detection section control circuits 52 and 54 and the heater section control circuits 53 and 55 for the first detection element 10 and the second detection element 20. However, the sensor control section 5 may be configured such that a single set including a detection section control circuit and a heater section control circuit is connected to the first detection element 10 and the second detection element 20 through a switch or the like, and is commonly used between the first and the second detection elements 10 and 20.

In the above-described embodiment, the detection apparatus 1 is connected to the input apparatus 58 and the display apparatus 59 via the input/output section 57 for allowing operation and display. However, the detection apparatus 1 may be connected to an unillustrated external circuit via the input/output section 57 so as to enable inputting of operation instructions from the external circuit and outputting of the detected concentrations of NO and $NO_2$ to the external circuit. Examples of such an external circuit include an electronic control unit (ECU) of an automobile and a personal computer (PC).

Example 1

An evaluation test was conducted in order to confirm that a difference in detection sensitivity arises for the concentration of $NO_2$ between the second detection element 20 having the reduction section 18 and the first detection element 10 not having a reduction section. The evaluation test was performed by use of the above-described evaluation apparatus and in accordance with the same procedure as that of the above-described sensitivity ratio obtaining processing. Specifically, NO model gases and $NO_2$ model gases having different NO concentrations and $NO_2$ concentrations, respectively, within a range of 0 to 100 ppm were selectively supplied to the first detection element 10 and the second detection element 20, and the output values (current values) of the first detection element 10 and the second detection element 20 at each concentration were obtained.

Figure 4:
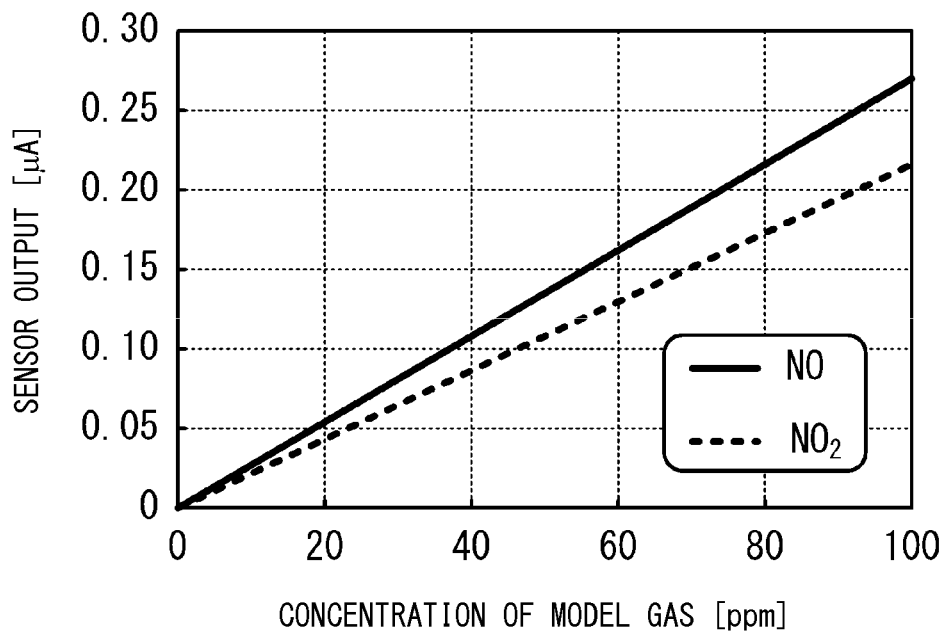
FIG. 4 is a graph showing the relation between the concentration of a model gas and the output value (current value) of the first detection element 10 having no reduction section.

FIG. 4 shows the relation between the concentration of the NO model gas and the $NO_2$ model gas and the output value (current value) of the first detection element 10 having no reduction section. In the case where the NO model gas (indicated by a solid line) is supplied to the first detection element 10, the output value of the first detection element 10 is proportional to the concentration of the NO model gas. Similarly, in the case where the $NO_2$ model gas (indicated by a broken line) is supplied to the first detection element 10, the output value of the first detection element 10 is proportional to the concentration of the $NO_2$ model gas. However, the test results show that the output value is smaller than that in the case where the NO model gas is supplied to the first detection element 10, and is about 80% that in the case where the NO model gas is supplied to the first detection element 10 at the same concentration. Specifically, whereas the output value of the first detection element 10 becomes 0.27 µA when an NO model gas whose concentration is 100 ppm is supplied to the first detection element 10, the output value of the first detection element 10 becomes 0.22 µA when an $NO_2$ model gas whose concentration is 100 ppm is supplied to the first detection element 10.

Figure 5:
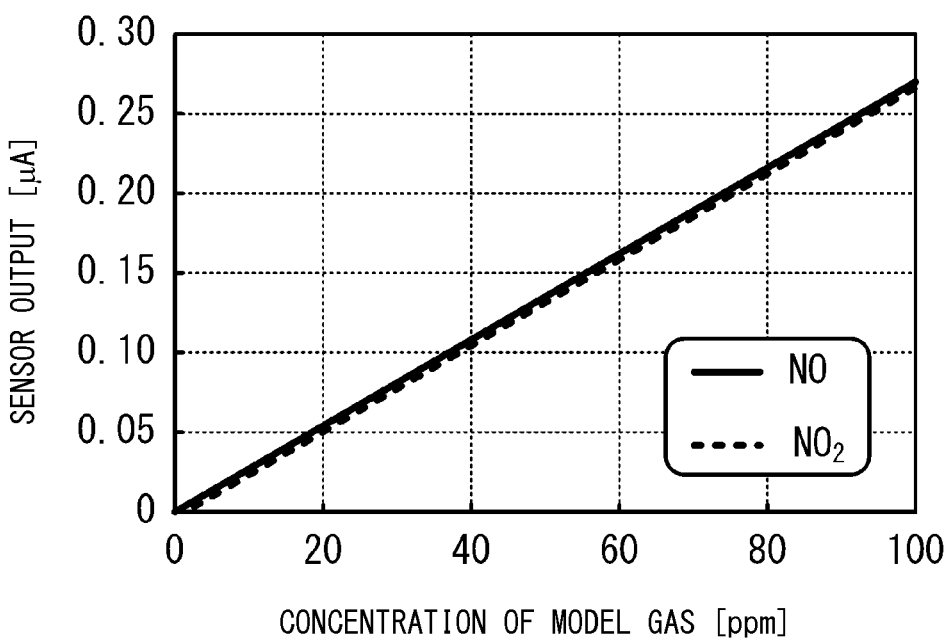
FIG. 5 is a graph showing the relation between the concentration of a model gas and the output value (current value) of the second detection element 20 having a reduction section 18.

FIG. 5 shows the relation between the concentration of the NO model gas and the $NO_2$ model gas and the output value (current value) of the second detection element 20 having the reduction section 18. In the case where the NO model gas (indicated by a solid line) is supplied to the second detection element 20, the output value of the second detection element 20 is proportional to the concentration of the NO model gas, as in the case of the first detection element 10. Similarly, in the case where the $NO_2$ model gas (indicated by a broken line) is supplied to the second detection element 20, the output value of the second detection element 20 is proportional to the concentration of the $NO_2$ model gas. However, the test results show that the output value is substantially equal to that obtained in the case where the NO model gas is supplied to the second detection element 20. Specifically, whereas the output value of the second detection element 20 becomes 0.27 µA when an NO model gas whose concentration is 100 ppm is supplied to the second detection element 20, the output value of the second detection element 20 also becomes 0.27 µA when an $NO_2$ model gas whose concentration is 100 ppm is supplied to the second detection element 20.

As described above, whereas the sensitivity of the first detection element 10 having no reduction section to $NO_2$ concentration is about 80% that of its sensitivity to NO concentration, the second detection element 20 has similar sensitivities to $NO_2$ concentration and to NO concentration because it has the reduction section 18. As a result, a difference in detection sensitivity for the $NO_X$ concentration can be provided between the first detection element 10 and the second detection element 20, and the detection apparatus 1 can obtain the concentrations of NO and $NO_X$ through use of the first detection element 10 and the second detection element 20.

Notably, in the present invention, the $NO_2$/NO sensitivity ratio of the first detection element 10 corresponds to the "first sensitivity ratio," and the $NO_2$/NO sensitivity ratio of the second detection element 20 corresponds to the "second sensitivity ratio." The first detection element 10 corresponds to the "first element section," and the second detection element 20 corresponds to the "second element section." The CPU of the microcomputer 51 which, in S23, obtains an NO concentration corresponding value (corresponding to the first concentration corresponding value) based on the output value (current value) of the first detection element 10 corresponds to the "first obtaining means (step)." Similarly, the CPU of the microcomputer 51 which, in S23, obtains an NO concentration corresponding value (corresponding to the second concentration corresponding value) based on the output value (current value) of the second detection element 20 corresponds to the "second obtaining means (step)." The CPU of the microcomputer 51 which, in S25, calculates the difference ΔC (corresponding to the concentration difference) between the NO concentration corresponding value of the first detection element 10 and the NO concentration corresponding value of the second detection element 20 corresponds to the "first calculation means (step)." The CPU of the microcomputer 51 which, in S26, calculates the difference ΔS (corresponding to the sensitivity difference) between the $NO_2$/NO sensitivity ratio of the first detection element 10 and the $NO_2$/NO sensitivity ratio of the second detection element 20, and calculates the $NO_2$ concentration corresponding value by dividing the difference ΔC by the difference ΔS corresponds to the "second calculation means (step)." The CPU of the microcomputer 51 which, in S27, calculates the NO concentration corresponding value corresponds to the "third calculation means (step)."

The diffusion resistor section 103 of the first detection element 10 corresponds to the "first diffusion resistor section," and the diffusion resistor section 103 of the second detection element 20 corresponds to the "second diffusion resistor section." The first and second measurement chambers 101 and 102 of the first detection element 10 correspond to the "first measurement chamber" and the "second measurement chamber," respectively, and the first and second measurement chambers 101 and 102 of the second detection element 20 correspond to the "third measurement chamber" and the "fourth measurement chamber," respectively. The solid electrolyte member 111 and the electrodes 112, 113 of the first detection element 10 correspond to the "first solid electrolyte layer" and the "pair of first electrodes," respectively, and the solid electrolyte member 111 and the electrodes 112, 113 of the second detection element 20 correspond to the "third solid electrolyte layer" and the "pair of third electrodes," respectively. The Ip1 cell 110 of the first detection element 10 corresponds to the "first oxygen pump cell," and the Ip1 cell 110 of the second detection element 20 corresponds to the "third oxygen pump cell." The solid electrolyte member 131 and the electrodes 132, 133 of the first detection element 10 correspond to the "second solid electrolyte layer" and the "pair of second electrodes," respectively, and the solid electrolyte member 131 and the electrodes 132, 133 of the second detection element 20 correspond to the "fourth solid electrolyte layer" and the "pair of fourth electrodes," respectively. The Ip2 cell 130 of the first detection element 10 corresponds to the "second oxygen pump cell," and the Ip2 cell 130 of the second detection element 20 corresponds to the "fourth oxygen pump cell." The heater conductor 151 of the second detection element 20 corresponds to the "heater." The detection section control circuit 52 corresponds to the "first element control section," and the detection section control circuit 54 corresponds to the "second element control section." The heater section control circuit 55 corresponds to the "heater control section".

The invention has been described in detail by reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2011-32651 filed Feb. 17, 2011, the disclosure of which is incorporated herein by reference in its entirety.

What is claimed is:
1. An $NO_X$ concentration detection apparatus comprising:
  a first element section through which current corresponding to a concentration of $NO_X$ in an object gas flows and which has a first sensitivity ratio between sensitivity to NO concentration and sensitivity to $NO_2$ concentration;
  a second element section comprising:

a second diffusion resistor section which is a porous body and restricts an amount of flow of the object gas, a reduction section which is a porous body and disposed on an upstream side of the second diffusion resistor section, said reduction section reducing $NO_2$ contained in the object gas to NO, and a heater for heating the reduction section, wherein the second element section is a second element section through which current corresponding to a concentration of $NO_X$ contained in the object gas flows and which has a second sensitivity ratio between sensitivity to NO concentration and sensitivity to $NO_2$ concentration, the second sensitivity ratio being greater than the first sensitivity ratio;

first obtaining means for obtaining a first concentration corresponding value which corresponds to a concentration of NO on a basis of a magnitude of the current flowing through the first element section;

second obtaining means for obtaining a second concentration corresponding value which corresponds to the concentration of NO on a basis of a magnitude of the current flowing through the second element section;

first calculation means for calculating a concentration difference, which is a difference between the first concentration corresponding value and the second concentration corresponding value;

second calculation means for calculating a sensitivity difference, which is a difference between the first sensitivity ratio and the second sensitivity ratio, and for calculating an $NO_2$ concentration corresponding value corresponding to the concentration of $NO_2$ in the object gas on a basis of the concentration difference and the sensitivity difference; and third calculation means for calculating an NO concentration corresponding value corresponding to the concentration of NO in the object gas on a basis of the first concentration corresponding value or the second concentration corresponding value, and the $NO_2$ concentration corresponding value, wherein a porosity of the reduction section is higher than that of the second diffusion resistor section.

2. The $NO_X$ concentration detection apparatus according to claim 1, wherein the first element section is a first detection element comprising a first measurement chamber into which the object gas is introduced via a first diffusion resistor section which restricts flow of the object gas therethrough, a first oxygen pump cell having a first solid electrolyte layer and a pair of first electrodes provided on inner and outer sides of the first measurement chamber, a second measurement chamber which is located downstream of the first measurement chamber and into which the object gas is introduced from the first measurement chamber, and a second oxygen pump cell having a second solid electrolyte layer and a pair of second electrodes provided on inner and outer sides of the second measurement chamber;

the second element section is a second detection element comprising a third measurement chamber into which the object gas is introduced via the second diffusion resistor section which restricts flow of the object gas therethrough, a third oxygen pump cell having a third solid electrolyte layer and a pair of third electrodes provided on inner and outer sides of the third measurement chamber, a fourth measurement chamber which is located downstream of the third measurement chamber and into which the object gas is introduced from the third measurement chamber, a fourth oxygen pump cell having a fourth solid electrolyte layer and a pair of fourth electrodes provided on inner and outer sides of the fourth measurement chamber, the reduction section provided upstream of the second diffusion resistor section, said reduction section reducing $NO_2$ contained in the object gas introduced into the third measurement chamber to NO, and the heater for heating the reduction section; and the $NO_X$ concentration detection apparatus comprises a first element control section which controls the first detection element, the first element control section controlling a supply of electric current to the first oxygen pump cell so as to pump out oxygen contained in the object gas introduced into the first measurement chamber or pump oxygen thereinto, to thereby control the oxygen concentration within the first measurement chamber to a constant level, and the first element control section applying a voltage to the second oxygen pump cell to thereby control decomposition of $NO_X$ contained in the object gas and pumping out of dissociated oxygen from the second measurement chamber, a second element control section which controls the second detection element, the second element control section controlling a supply of electric current to the third oxygen pump cell so as to pump out oxygen contained in the object gas introduced into the third measurement chamber or pump oxygen thereinto, to thereby control the oxygen concentration within the third measurement chamber to a constant level, and the second element control section applying a voltage to the fourth oxygen pump cell to thereby control decomposition of $NO_X$ contained in the object gas and pumping out of dissociated oxygen from the fourth measurement chamber, and a heater control section which supplies a drive current to the heater so as to heat the object gas flowing through the reduction section at least to a reduction temperature required for reducing $NO_2$ to NO.

3. A method for detecting $NO_X$ concentration including obtaining concentrations of NO and $NO_2$ contained in an object gas, which method is executed by a microcomputer provided in a detection apparatus which includes two element sections having different sensitivity ratios, each being a ratio between sensitivity to concentrations of NO and $NO_2$ contained in the object gas, said method comprising:

obtaining a first concentration corresponding value corresponding to the concentration of NO on a basis of a magnitude of current flowing through a first element section having a first sensitivity ratio;

obtaining a second concentration corresponding value corresponding to the concentration of NO on a basis of a magnitude of current flowing through a second element section having a second sensitivity ratio greater than the first sensitivity ratio;

calculating a concentration difference, which is a difference between the first concentration corresponding value and the second concentration corresponding value;

calculating a sensitivity difference, which is a difference between the first sensitivity ratio and the second sensitivity ratio, and calculating an $NO_2$ concentration corresponding value corresponding to the concentration of $NO_2$ contained in the object gas on a basis of the concentration difference and the sensitivity difference; and calculating an NO concentration corresponding value corresponding to the concentration of NO contained in the object gas on a basis of the first concentration corresponding value or the second concentration corresponding value, and the $NO_2$ concentration corresponding value, wherein the second element section comprises:

a second diffusion resistor section which is a porous body and restricts an amount of flow of the object gas, a reduction section which is a porous body and disposed on an upstream side of the second diffusion resistor section, said reduction section reducing $NO_2$ contained in the object gas to NO, and a heater for heating the reduction section; and wherein a porosity of the reduction section is higher than that of the second diffusion resistor section.

* * * * *